United States Patent
Tas

(10) Patent No.: US 11,810,579 B2
(45) Date of Patent: Nov. 7, 2023

(54) SYSTEMS AND METHODS FOR TRACKING BIOMARKERS IN SUBJECTS

(71) Applicant: NEUROPATH SPRL, Louvain-la-Neuve (BE)

(72) Inventor: Benoit Yvonne Tas, Heverlee (BE)

(73) Assignee: NEUROPATH SPRL, Enghien (BE)

( * ) Notice: Subject to any disclaimer, the term of this patent is extended or adjusted under 35 U.S.C. 154(b) by 0 days.

(21) Appl. No.: 16/696,534

(22) Filed: Nov. 26, 2019

(65) Prior Publication Data

US 2020/0098376 A1   Mar. 26, 2020

Related U.S. Application Data

(63) Continuation-in-part of application No. 15/984,986, filed on May 21, 2018, now Pat. No. 10,485,454.

(60) Provisional application No. 62/510,749, filed on May 24, 2017.

(51) Int. Cl.
| | |
|---|---|
| *G10L 17/26* | (2013.01) |
| *G16H 50/30* | (2018.01) |
| *G16H 50/20* | (2018.01) |
| *G10L 21/06* | (2013.01) |
| *A61B 5/00* | (2006.01) |
| *G10L 25/03* | (2013.01) |
| *G10L 25/60* | (2013.01) |
| *G10L 25/66* | (2013.01) |
| *G10L 13/02* | (2013.01) |

(52) U.S. Cl.
CPC ............ *G10L 17/26* (2013.01); *A61B 5/0004* (2013.01); *G10L 13/02* (2013.01); *G10L 21/06* (2013.01); *G10L 25/03* (2013.01); *G10L 25/60* (2013.01); *G10L 25/66* (2013.01); *G16H 50/20* (2018.01); *G16H 50/30* (2018.01)

(58) Field of Classification Search
CPC ......... G10L 17/26; G10L 13/02; G10L 21/06; G10L 25/03; G10L 25/60; G10L 25/66; G16H 50/30; G16H 50/20; A61B 5/0004
See application file for complete search history.

(56) References Cited

U.S. PATENT DOCUMENTS

| | | | |
|---|---|---|---|
| 9,342,829 B2 * | 5/2016 | Zhou | G06Q 20/3829 |
| 9,579,056 B2 * | 2/2017 | Rosenbek | A61B 5/7275 |
| 10,249,305 B2 * | 4/2019 | Yu | G10L 19/022 |

(Continued)

*Primary Examiner* — Gregory M Desire

(57) ABSTRACT

A system for tracking biomarkers in subjects. In one embodiment, the biomarker tracking system has a sensory array including an RGB-D camera or RGB camera, a memory, and an electronic processor. The microphone captures voice data, including but not limited to tremor detection data, speech volume and pronunciation data, speech strength data, changes in tonality, hesitance in voice, and changes in speed or verbiage. A stored baseline biomarker model may comprise a voice data profile which may be pre-stored in the memory of a server and include a plurality of benchmarks. This electronic processor is configured to use this pre-stored voice data and compare it to the voice data captured with the microphone. The electronic processor is further configured to determine a set of attributes for the voice data, and generates a speech data deviation model based, at least in part, on the comparison of the speech data to the stored baseline biomarker model.

20 Claims, 5 Drawing Sheets

(56) References Cited

U.S. PATENT DOCUMENTS 10,748,644 B2* 8/2020 Shriberg ................ G16H 15/00
2018/0296092 A1* 10/2018 Hassan .................. G10L 25/66

* cited by examiner

SYSTEMS AND METHODS FOR TRACKING BIOMARKERS IN SUBJECTS

RELATED APPLICATIONS

This application claims priority to U.S. Nonprovisional application Ser. No. 15/984,986, entitled "Systems and Methods for Markerless Tracking of Subjects", filed May 21, 2017, which claims priority to U.S. Provisional Application No. 62/510,749, entitled "Methods and System for Assessing Neurological Disease", filed May 24, 2017. The entire contents of these two applications are incorporated herein by reference.

BACKGROUND

Degenerative diseases affect millions of people worldwide. Parkinson's disease, for example, affects between 5 and 7 million people, and is the second largest neurological disease. To track the progression of degenerative diseases, subjects are periodically evaluated by medical professionals using established rating scales. An example rating scale for Parkinson's disease is the Movement Disorder Society unified Parkinson's disease rating scale (MDS-UPDRS). As explained below, the current examination methods for subjects with Parkinson's disease (and other neurological diseases) have several significant limitations.

Currently, examinations of subjects are performed by doctors during office visits. Subjects with Parkinson's disease typically visit a doctor's office once or twice a year. Thus, their condition is only monitored 1 to 2 hours per year. This leaves about 8,765 hours per year when their condition is not being monitored.

Established rating scales (such as the MDS-UPDRS) typically include questionnaires and an evaluation of vocal characteristics. Currently, a doctor listens to a subject performing each of a series of vocal exercises and then determines a rating for the subject's voice characteristics based on a series of prescribed guidelines. Many of the prescribed guidelines are subjective and open to the interpretation of the doctor performing the examination. For example, a prescribed guideline may require the doctor to differentiate between subjects exhibiting minor vocal stuttering verses subjects with substantial vocal stuttering. In addition, many of the prescribed guidelines require the doctor to evaluate attributes that are difficult to discern without advanced equipment. For example, a prescribed guideline may require the doctor to differentiate the loudness of ordinary speech, for differences around 10 decibels.

Further, Parkinson's disease is a very individual disease. Every subject develops different motor and non-motors symptoms at different rates. The currently examination methods employ fixed rating scales that do not account for the symptom development of individual subjects.

SUMMARY

The disclosure provides a system for tracking biomarkers in a Parkinson's patient. In one embodiment, the system has a sensory array including an RGB-D or RGB camera, a memory, and an electronic processor. The microphone captures voice data, including but not limited to tremor detection data, speech volume and pronunciation data, speech strength data, changes in tonality, hesitance in voice, and changes in speed or verbiage. A stored baseline biomarker model may comprise a voice data profile which may be pre-stored in the memory of a server and include a plurality of benchmarks. This electronic processor is configured to use this pre-stored voice data and compare it to the voice data captured with the microphone. The electronic processor is further configured to determine a set of attributes for the voice data, and generates a speech data deviation model based, at least in part, on the comparison of the speech data to the stored baseline biomarker model.

In some embodiments, objective data may be captured at least in part using another type of camera or image capture device, for example a smart phone camera or a depth-sensitive image capture device. In some embodiments, objective data may be captured in part using cognitive games or other interactive activities of a patient.

In some embodiments, the electronic processor is also configured to generate a disease state report based at least in part on the speech data deviation model. In other embodiments, the disease state report is automatically reported to a third party. In still other embodiments, generating the disease state report further comprises receiving responses to a questionnaire, which is collected by the electronic processor. In some embodiments the questionnaire may include one or more of medication intake timing, reported sleep data, and reported physical exercise. In some embodiments the baseline biomarker model comprises previously collected data associated with the patient while in other embodiments, the baseline biomarker data comprises speech data of a cohort of the subject. In some embodiments the baseline biomarker model is updated using one or more of the collected speech data of the subject in addition to the speech deviation model. In still other embodiments, the electronic processor collects data over at least one week.

According to some embodiments, the system may detect and/or track significant "events" in the patient data. For example, changes in sleep patterns or changes in physical, mental, or social parameters associated with a patient may be detected and tracked as noteworthy events that may be studied further. According to some embodiments, events may include deviations from a patient's baseline motor, non-motor, or emotional state. In some embodiments, events may include deviations from a prescribed care path, such as when a system detects that a patient is not getting prescribed physical activity or following a prescribed medication schedule.

According to some embodiments, significant events may be detected by analysis of other parameters. For example, a system may detect correlations between parameters. As one example, it may be considered medically significant that a patient experiences more of a specific kind of motor difficulty—or motor symptoms in general—when the patient has not slept well, as determined by self-reporting and/or sleep monitoring devices. As another example, the system may find a correlation between a patient feeling more depressed during times when the patient's social contacts are deteriorating. In some embodiments, certain such events and correlations may be specified for monitoring by a physician or patient. In some embodiments, a system may unilaterally detect events and/or correlations and choose which ones to track or report, for example by applying machine learning or other computing techniques to the gathered data.

The disclosure further provides a method for tracking biomarkers in a Parkinson's patient. The method includes storing a baseline biomarker model which may comprise a voice data profile including a plurality of benchmarks. The method further includes capturing voice data, including but not limited to tremor detection data, speech volume and pronunciation data, speech strength data, changes in tonality, hesitance in voice, and changes in speed or verbiage. The method further includes collecting the captured voice data, accessing the stored baseline biomarker model, and comparing the captured voice data to the stored baseline biomarker model. The method further includes generating a speech data error recognition percentage. In some embodiments, the method includes generating a disease state report by comparing the collected and stored data. In other embodiments, the method further includes collecting a questionnaire by an electronic processor as data in generation of the disease report. In some embodiments, the method includes generating a disease state report which includes linking voice parameters to other motor data such as medication intake timing, reported sleep data, and reported physical exercise collected by the questionnaire. In still other embodiments, the method includes engaging in adaptive learning based on the linked voice parameters and other motor data. In some embodiments, the method includes collecting data over at least one week. In other embodiments, the method further includes automatically reporting the state report to a third party. In still other embodiments, the method further includes building a baseline profile using the complete disease state report, and in some embodiments the method includes monitoring the progression of a disease by detecting when data thresholds specific to a user's baseline profile are surpassed.

Other aspects and embodiments will become apparent by consideration of the detailed description and accompanying drawings.

Figure 1:
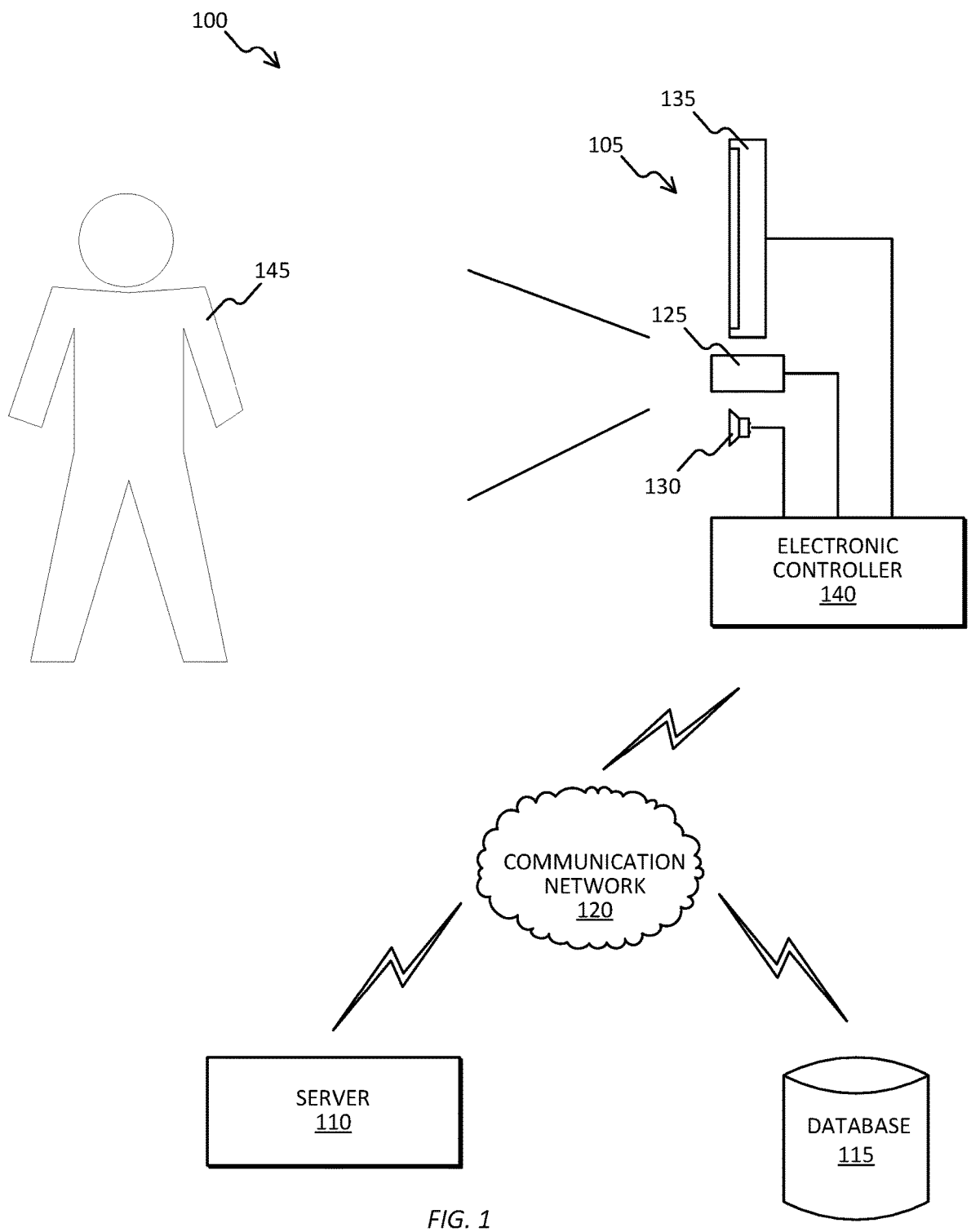
FIG. 1 is a diagram of a biomarker tracking system, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments illustrated.

The apparatus and method components have been represented where appropriate by conventional symbols in the drawings, showing only those specific details that are pertinent to understanding various embodiments so as not to obscure the disclosure with details that will be readily apparent to those of ordinary skill in the art having the benefit of the description herein.

DETAILED DESCRIPTION

Before any embodiments are explained in detail, it is to be understood that no embodiment is necessarily limited in its application to the details of construction and the arrangement of components set forth in the following description or illustrated in the following drawings. Other embodiments are possible and embodiments described are capable of being practiced or of being carried out in various ways.

It should also be noted that a plurality of different structural components may be utilized to implement the disclosure. Furthermore, and as described in subsequent paragraphs, the specific configurations illustrated in the drawings are intended to exemplify certain embodiments. Alternative configurations are possible.

For ease of description, the example systems presented herein may be illustrated with a single exemplar of each of their component parts. Some examples may not describe or illustrate all components of the systems. Other example embodiments may include more or fewer of each of the illustrated components, may combine some components, or may include additional or alternative components.

FIG. 1 is a diagram of one example embodiment of a biomarker tracking system 100. In the embodiment illustrated in FIG. 1, the biomarker tracking system 100 includes an electronic tracking device 105, a server 110, a database 115, and a communication network 120. The electronic tracking device 105 is illustrated in FIG. 1 as a combination of a sensor array 125, a speaker 130, a display screen 135, and an electronic controller 140. As described in more detail below, the electronic tracking device 105 records and evaluates, among other things, different types of speech data for a subject (for example, user 145 in FIG. 1).

The communication network 120 may be a wired network, a wireless network, or both. All or parts of the communication network 120 may be implemented using various networks, for example, a cellular network, the Internet, a Bluetooth™ network, a wireless local area network (for example, Wi-Fi), a wireless accessory Personal Area Networks (PAN), cable, an Ethernet network, satellite, a machine-to-machine (M2M) autonomous network, and a public switched telephone network. The electronic tracking device 105, the server 110, and the other various components of the biomarker tracking system 100 communicate with each other over the communication network 120 using suitable wireless or wired communication protocols. In some embodiments, communications with other external devices (not shown) occur over the communication network 120.

The biomarker tracking system 100 illustrated in FIG. 1 is provided as one example of such a system. The methods described herein may be used with tracking systems with fewer, additional, or different components in different configurations than the biomarker tracking system 100 illustrated in FIG. 1. For example, in some embodiments, the biomarker tracking system 100 includes fewer or additional electronic tracking devices, fewer or additional servers, and fewer or additional databases.

Figure 2:
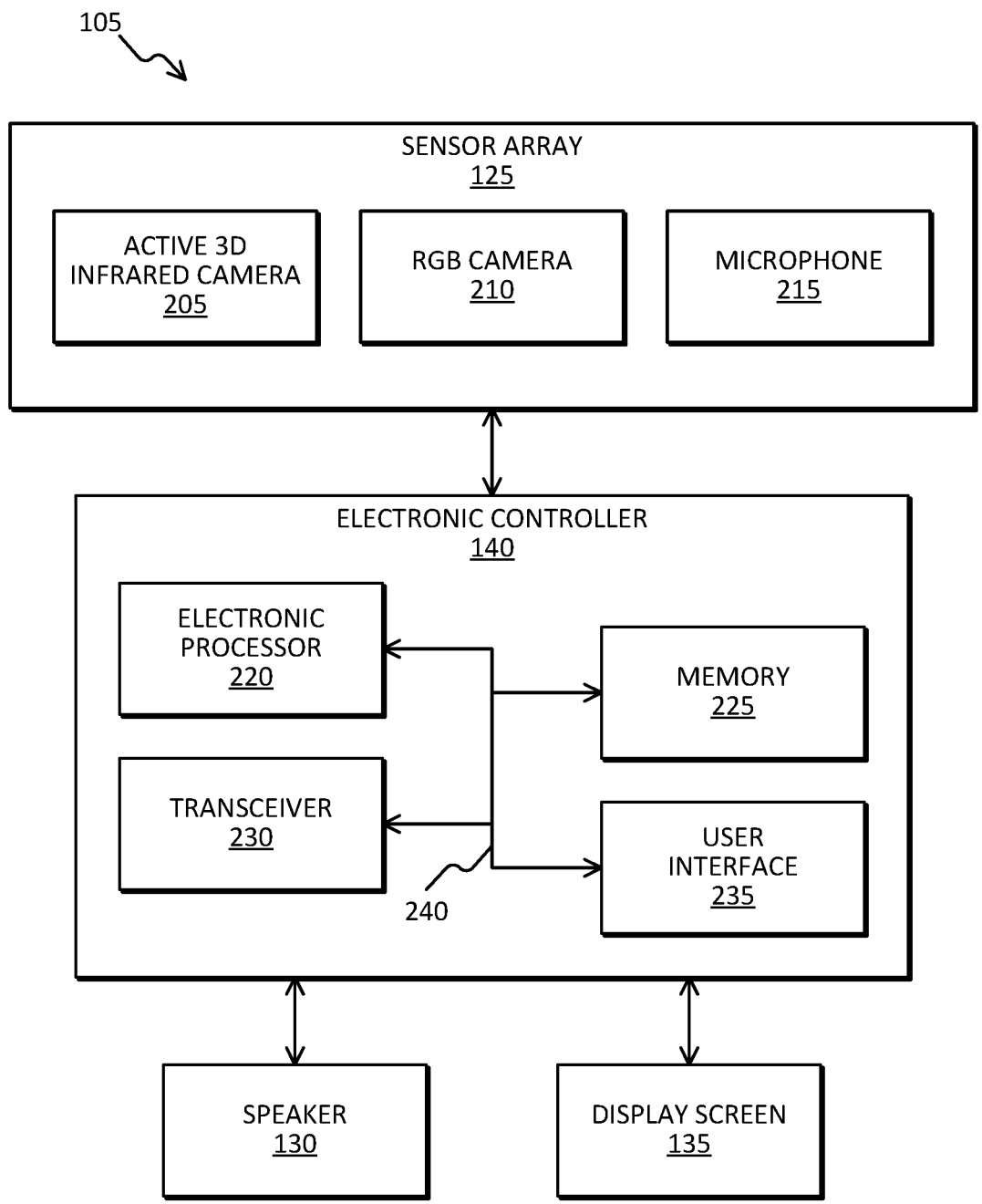
FIG. 2 is a diagram of an electronic tracking device included in the biomarker tracking system of FIG. 1, in accordance with some embodiments.

FIG. 2 is a diagram of one example embodiment of the electronic tracking device 105 including the sensor array 125, the speaker 130, the display screen 135, and the electronic controller 140. In alternate embodiments, the electronic tracking device 105 may include fewer or additional components in configurations different from the configuration illustrated in FIG. 2.

The sensor array 125 illustrated in FIG. 2 includes an RGB-D camera 205, and a red-green-blue (RGB) camera 210, and a microphone 215. In some embodiments, the RGB-D or infrared camera 205, the RGB camera 210, and the microphone 215 are commonly located in the same sensory array housing, as illustrated in FIGS. 1 and 2. Alternatively, RGB-D camera 205, the RGB camera 210, and the microphone 215 may be located in separate housings.

The microphone 215 is a transducer which captures acoustical energy and converts this into an electrical signal. The microphone 215 includes a diaphragm which vibrates upon being struck by sound waves, and these vibrations cause other components in the microphone 215 to vibrate. These vibrations are then captured and converted into an electrical signal. This captured acoustical energy after conversion to an electrical signal is stored as speech data, which is then used to help diagnose the patient.

The microphone 215 may utilize any of a plurality of techniques to convert sound into electricity, including but not limited to dynamic or condenser technologies. In a dynamic microphone, the vibration of the microphone causes a coil to move back and forth near a magnet, which creates a current in the coil which is channeled from the microphone along wires to create the electrical signal. In a condenser microphone, a capacitor with two plates inside of the microphone uses one of them as the diaphragm to vibrate when struck with acoustical energy. This vibration causes the plates to move closer and farther away, as one plate is stationary while the other vibrates, causing a current to flow while a voltage is applied to the capacitor. Either of these technologies may be used in the microphone 215 to convert the acoustical energy into an electrical signal, and in other embodiments other technologies may be used, such as ribbon or crystal technologies, or any of the other conversion technologies known by one skilled in the art. Examples of microphones 215 which may be used in the biomarker tracking system 100 include but are not limited to Kinect™ by Microsoft™, the Intel™ Smart Sount Technology, the Insten 3.5 mm Studio Professional Microphone, and the Technical Pro MK75.

The microphone 215 enables non-obtrusive body motion tracking of a subject without markers. Some other systems for tracking the well-being of patients require placing a plurality of markers on a subject's body. However, marker-based body tracking systems have several drawbacks. Placing the markers on the subject's body is time-consuming. In addition, subjects with neurological diseases typically suffer from motor impairments which make it difficult for them to attach markers to their bodies without assistance. Further, the presence of markers on the subject's body while the subject is performing vocal exercises can alter the subject's movements. Capturing audio data requires none of these drawbacks, and takes far less time than a marker based tracking system. Additionally, this microphone 215 can run in the background unimpeded, being able to collect speech data for long periods of time in a non-intrusive manner. To ensure that excess power is not being used by running all the time, in some embodiments, the microphone 215 may include a sleep function wherein after a set period of time not picking up any acoustical energy, the microphone goes into a sleep state.

The microphone 215 detects sound and outputs analogous electric signals representing the sound to the electronic controller 140. The speaker 130 receives electric signals from the electronic controller 140 and outputs sound. The display screen 135 displays visual output generated by software applications executed by the electronic controller 140. Visual output includes, for example, graphical indicators, lights, colors, text, images, internet webpages, graphical user interfaces (GUIs), combinations of the foregoing, and the like. The display screen 135 includes a suitable display mechanism for displaying the visual output (for example, a light-emitting diode (LED) screen, a liquid crystal display (LCD) screen, an organic LED (OLED) screen, and the like).

The electronic controller 140 illustrated in FIG. 2 includes an electronic processor 220 (for example, a microprocessor), a memory 225, a transceiver 230, and a user interface 235. The electronic processor 220, the memory 225, as well as the other various modules are coupled by a bus 240, or are coupled directly, by one or more additional control or data buses, or a combination thereof. The memory 225 may include read only memory (ROM), random access memory (RAM), other non-transitory computer-readable media, or a combination thereof. The electronic processor 220 is configured to retrieve program instructions and data from the memory 225 and execute, among other things, instructions to perform the methods described herein.

The transceiver 230 transmits signals to the communication network 120 and receives signals from the communication network 120. Signals may include, for example, information, data, serial data, data packets, analog signals, or a combination thereof. The transceiver 230 can be coupled to one or more separate transceivers via wires, fiber, wirelessly, or a combination thereof. In some embodiments, the transceiver 230 includes separate transmitters and receivers.

The user interface 235 is included to control the electronic tracking device 105 or the operation of the biomarker tracking system 100 as a whole. The user interface 235 can include any combination of digital and analog input devices required to achieve a desired level of control for the system. In some embodiments, the user interface 235 includes a touch sensitive interface. For example, in some embodiments, the display screen 135 is a touch-screen display that receives user input using detected physical contact (for example, detected capacitance or resistance). Based on the user input, the display screen 135 outputs signals to the electronic processor 220 which indicate positions on the display screen 135 currently being selected by physical contact. Alternatively or in addition, the user interface 235 receives user input from a plurality of input devices such as a keyboard, a mouse, a trackpad, the microphone 215, and the like. In some constructions, the user interface 235 is separated from the electronic controller 140.

Figure 3:
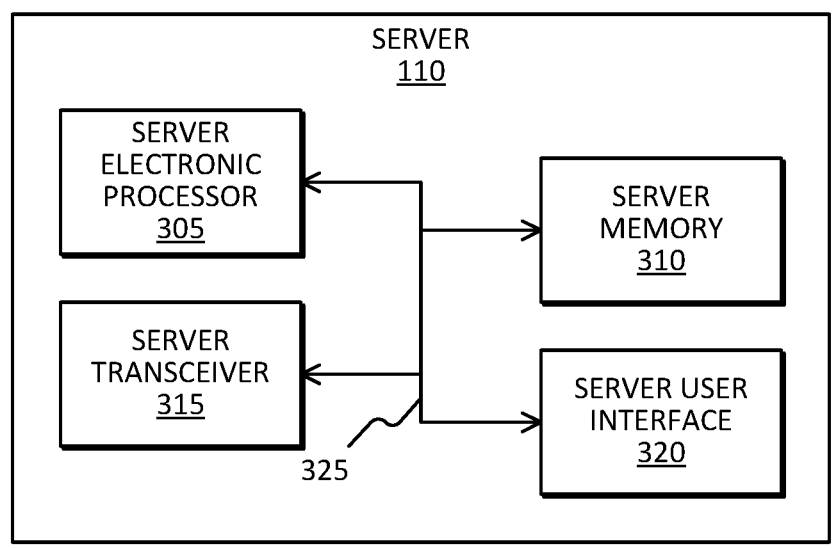
FIG. 3 is a diagram of a server included in the biomarker tracking system of FIG. 1, in accordance with some embodiments.

FIG. 3 is a diagram of one example embodiment of the server 110. In the example illustrated, the server 110 includes a server electronic processor 305, server memory 310, a server transceiver 315, and a server user interface 320. The server electronic processor 305, the server memory 310, as well as the other various modules are coupled by a bus 325, or are coupled directly, by one or more additional control or data buses, or a combination thereof. In other embodiments, the server 110 may include fewer or additional components in configurations different from that illustrated in FIG. 3.

The server memory 310 stores program instructions and data. The server memory 310 may include combinations of different types of memory, including the various types of memory described above with respect to the memory 225 included in the electronic tracking device 105. The server electronic processor 305 retrieves program instructions from the server memory 310 and executes the instructions to perform a set of functions including all or part of the methods described herein. The server transceiver 315 transmits signals to and receives signals from the electronic tracking device 105 and the other components included in the biomarker tracking system 100, such as through the communication network 120 or directly. The server user interface 320 includes any combination of digital and analog input devices required to achieve a desired level of control for the server 110. For example, the server user interface 320 can include a computer having a display and input devices, a display, a keyboard, a mouse, speakers, and the like.

In some embodiments, the database 115 may include components or combinations of different components, including all or some of the various components described above with respect to the server 110.

As discussed above, established rating scales for subjects with Parkinson's disease (or other neurological diseases) typically include scores for a series of vocal exercises. Currently, a doctor listens to a subject performing each of the vocal exercises and then determines a rating for the subject's speech based on a series of prescribed guidelines. However, there is a need for a reliable system of capturing and objectively evaluating a subject's performance of vocal exercises without requiring a doctor to be present. As described below in more detail, the biomarker tracking system 100 records and automatically evaluates a subject's performance of a vocal exercise. Additionally, the biomarker tracking system 100 can record and save speech data to be used to evaluate a subject over longer periods of time, rather than during a performance of a vocal exercise such as during everyday speech in an area close to the microphone 215 of the biomarker tracking system 100.

Figure 4:
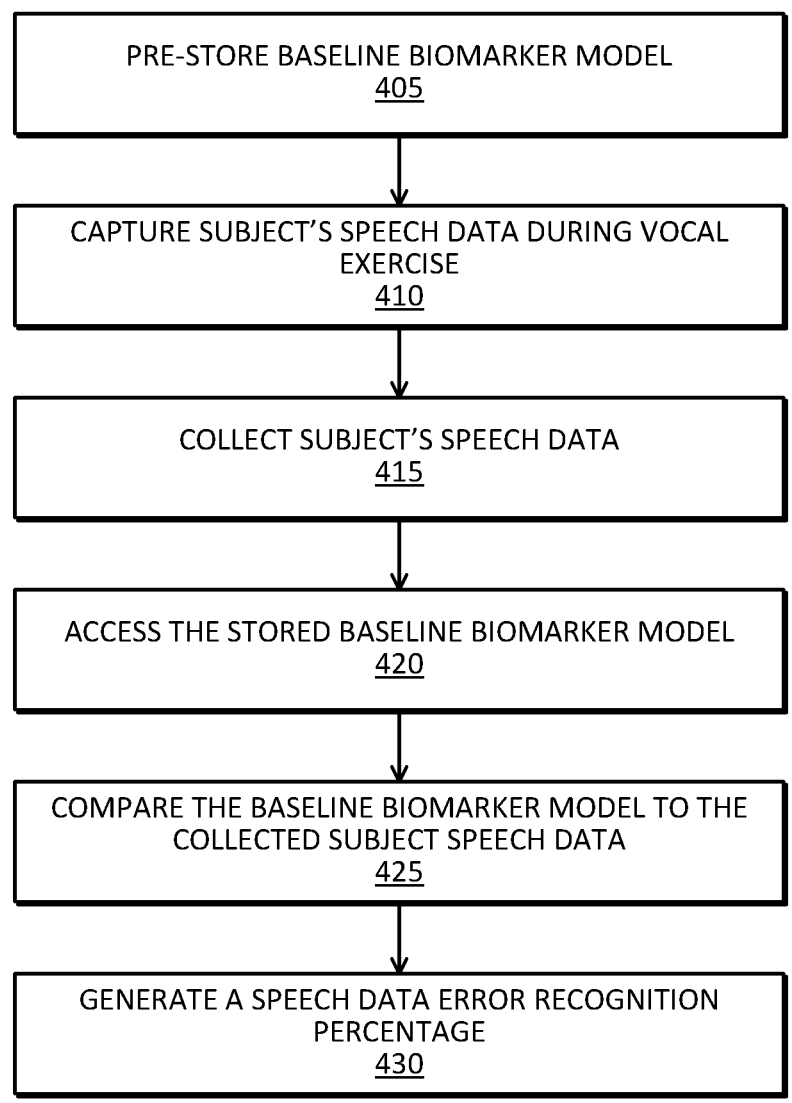
FIG. 4 is a flowchart of a method for tracking biomarkers with the electronic device of FIG. 2, in accordance with some embodiments.

FIG. 4 is an example embodiment of a method 400 for biomarker tracking of a subject performing a vocal exercise. At block 405, a baseline biomarker profile is pre-stored, for example, in the memory 225 of the electronic controller 140. The baseline biomarker profile includes a plurality of benchmarks for at least one vocal exercise. Each benchmark defines a set of conditions and a rating for a vocal exercise that are associated with a specific disease degeneration level. For example, a speech pattern with 1-2 voice tremors per vocal exercise may equate to a first degeneration level, whereas a speech pattern with 3-4 voice tremors per vocal exercise may be associated with a second degeneration level.

The baseline biomarker profile may be generated based on established rating scales. In some embodiments, the plurality of benchmarks included in the baseline biomarker profile are standard benchmarks that apply to all subjects with a specific neurological disease. Alternatively or in addition, the plurality of benchmarks included in the baseline biomarker profile are specifically tailored to the subject. In some embodiments, the baseline biomarker profile includes benchmarks for a plurality of vocal exercises. In some embodiments, the electronic controller 140 obtains the baseline biomarker profile (or a portion thereof) from the server 110, the database 115, or both.

At block 410, the microphone 215 captures speech data of a subject's voice while the subject is performing the vocal exercise. As described above, the speech data includes acoustical energy transformed into an electrical signal representing the speech pattern of the individual subject. The speech data may include tremor detection data, speech volume and pronunciation data, and speech strength data. Voice tremors are rhythmic involuntary oscillating movements that are common symptoms of neurologic disorders, and cause a fluctuation in the amplitude and fundamental frequency of the voice. Tremor detection data includes detecting these fluctuations in amplitude and frequency for the specific speech patterns of the subject performing the vocal exercise. Detecting speech strength and volume data may be done by picking up decibels of the subject's speech, and pronunciation data may be determined by comparing the speech of the subject to a pronunciation of a subject with a similar accent or manner of speaking.

At block 415, the electronic processor 220 collects the subject's speech data from everything stored in the memory 225 of the electronic controller 140 or any other speech data that the electronic processor 220 has access to. The speech data may include speech data from previous vocal exercises, as well as everyday speech in an area close to the microphone 215 of the biomarker tracking system 100 which was picked up passively rather than actively during a vocal exercise.

In some embodiments, the electronic processor 220 uses a plethora of approaches to determine the set of attributes for the detected vocal patterns of the subject's speech. As a first example, the electronic processor 220 determines a speed attribute for a certain vocal exercise in which the subject repeats a set or series of words as fast as possible. The electronic processor 220 may also determine a volume or strength attribute for other vocal exercises in which the subject repeats a set or series of words in increasing volume. The electronic processor 220 may also determine a tremor detection attribute in certain vocal exercises in which the subject repeats a set or series of words in real time, and again at a slower pace with specific pronunciations to detect a pronunciation attribute of the speech data particular to the individual patient.

The electronic processor 220 may assign a rating to the vocal exercise by comparing the set of attributes for the speech data of the subject to the plurality of benchmarks included in the pre-stored baseline biomarker profile. As described above, each benchmark defines a set of conditions and a rating for a vocal exercise that are associated with a specific mobility level. In some embodiments, the electronic processor 220 compares the set of attributes to the set of conditions and determines the lowest speech rating with at least one condition met by the set of attributes. For example, if a subject was assigned a high rating in both speech volume data and strength data, but obtained a low rating in pronunciation, the subject may be given the lower rating for purposes of diagnoses.

The electronic processor 220 may create a session record for the subject. The session record is a collection of data which provides various information about a subject's performance of a vocal exercise. The session record is stored (for example, in the memory 225, in the server memory 310, or in the database 115) such that it can be later accessed for review, analysis, or comparison to other session records. In some embodiments, the session record may be combined with other information of the subject that is included in an electronic health record (EHR).

Returning to FIG. 4, at block 420, the electronic processor 220 accesses the stored baseline biomarker data from the external server 110. As mentioned above, this baseline biomarker data may include speech data from previous vocal exercises, as well as everyday speech in an area close to the microphone 215 of the biomarker tracking system 100. Stored baseline biomarker data may also include ratings for past speech data, as well as the rating of speech of patients from each stage of vocal degeneration.

At block 425, the electronic processor 220 compares the baseline biomarker model to the collected subject speech data from the vocal exercise. The compared data may be measured against speech benchmarks, and may include benchmarks for tremor detection data, speech volume and pronunciation data, and speech strength data. This comparison simultaneously updates the baseline biomarker model, by including the new speech data from the vocal exercise into the baseline biomarker model. This inclusion of new speech data and formulation of the baseline biomarker model may be done by a machine learning process, which in some embodiments may be an unsupervised machine learning process. In some embodiments, the machine learning process includes adding weights to data, such that newer data that was more recently acquired is weighed more heavily than older data when deciding the current state of the subject of the vocal exercise.

At block 430, the electronic processor 220 generates a speech data error recognition percentage based on the comparison of the baseline biomarker model and the vocal exercise speech data. This speech data error recognition percentage is primarily based off of the tremor detection data, speech volume and pronunciation data, and speech strength data recorded by the microphone 215 during the vocal exercises. In the case of a vocal exercise being performed in front of a human physician, all of these attributes would be incredibly difficult to compare simultaneously to a baseline. Additionally, there would be no way to include passively monitored data over long periods of time which more accurately characterize a patient's everyday speech.

Figure 5:
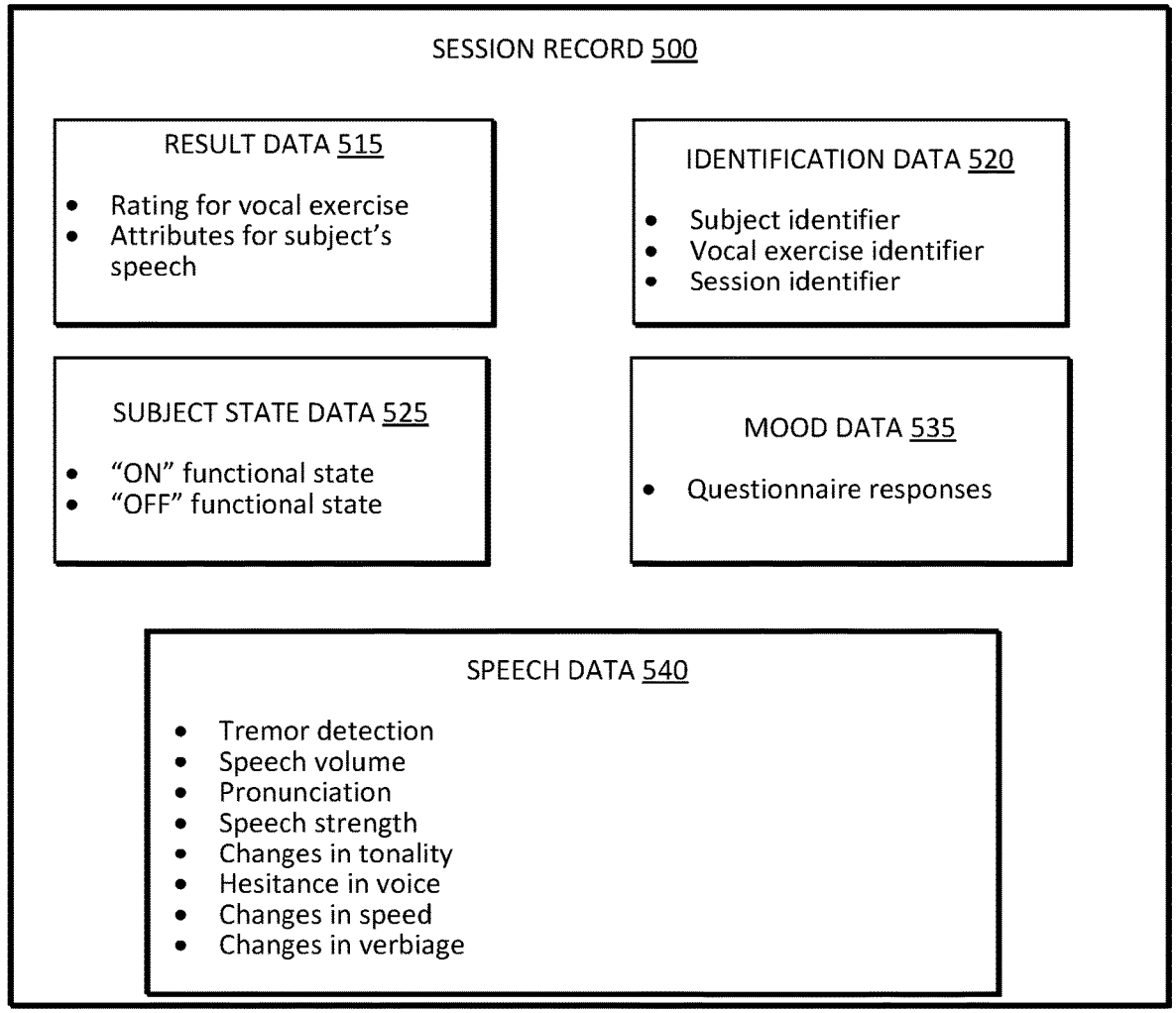
FIG. 5 is a diagram of session record created by the electronic tracking device of FIG. 2, in accordance with some embodiments.

FIG. 5 is a diagram of one example embodiment of a session record 500 for a subject. In the example illustrated in FIG. 5, the session record 500 includes result data 515, identification data 520, subject state data 525, mood data 535, and speech data 540. In other embodiments, a session record may include fewer or additional components in configurations different from that illustrated in FIG. 5.

The result data 515 includes, among other things, the rating for the vocal exercise assigned by the electronic processor 220, the set of attributes determined by the electronic processor 220, or a combination thereof. The result data is strictly confined to data resulting from performance of the vocal exercises, and does not include speech data collected over long periods of time.

The identification data 520 includes, among other things, a subject identifier, a vocal exercise identifier, a session identifier, or a combination thereof. The subject identifier identifies the subject performing the vocal exercise. The subject identifier may include, for example, a unique identification number assigned to the subject, the subject's name, the subject's date of birth, the subject's gender, the subject's telephone number, the subject's e-mail address, or a combination thereof. The vocal exercise identifier indicates the specific vocal exercise performed by the subject. For example, one vocal exercise identifier can indicate that the subject is performing a speech strength exercise and another vocal exercise identifier can indicate that the subject is performing a pronunciation exercise. In some embodiments, one session record can include data for multiple vocal exercises performed by the subject in a single session. For example, the subject may sequentially perform several vocal exercises in a single session. In such embodiments, the identification data 520 may include separate vocal exercise identifier for each vocal exercise performed by the subject. The session identifier differentiates one session record from another. The session identifier may include, for example, a unique identification number for the session, a time stamp, or both.

Subjects with neurological diseases, such as Parkinson's disease, often experience decreased vocal functionality over time. The decreased vocal functionality can be tracked by comparing measured attributes of vocal exercises from different session records. In addition, subjects with neurological diseases typically take medication to limit mobility symptoms. The session records may also be used to determine the effect of different medications on the mobility of a patient.

Subjects with neurological diseases often have periods of time in which their mobility is impaired in spite of taking medication. A subject is considered to be in an ON functional state when they are taking medication and having a good response. A subject is considered to be in an OFF functional state when they are having a poor response in spite of taking medication. The subject state data 525 indicates whether the subject is in the ON functional state or in the OFF functional state while performing the vocal exercise. In some embodiments, the electronic processor 220 determines the subject's functional state by comparing the set of attributes determined for the subject's current performance of the vocal exercise with a set of attributes determined for a prior performance of the vocal exercise by the subject. In some embodiments, the electronic processor 220 may retrieve the set of attributes determined for the subject's prior performance of the vocal exercise (for example, a second set of attributes) from the memory 225. The electronic processor 220 determines whether the subject is in the ON functional state or in the OFF functional state based on a difference between the set of attributes determined for the subject's current performance of the vocal exercise and the second set of attributes. For example, a large deviation between the speech volume data for the most recent vocal exercise and the speech volume data for a prior performance of the vocal exercise may indicate that the subject is in the OFF functional state.

According to some embodiments, the system may detect and/or track significant "events" in the patient data. For example, changes in sleep patterns or changes in physical, mental, or social parameters associated with a patient may be detected and tracked as noteworthy events that may be studied further. According to some embodiments, events may include deviations from a patient's baseline motor, non-motor, or emotional state. In some embodiments, events may include deviations from a prescribed care path, such as when a system detects that a patient is not getting prescribed physical activity or following a prescribed medication schedule.

According to some embodiments, significant events may be detected by analysis of other parameters. For example, a system may detect correlations between parameters. As one example, it may be considered medically significant that a patient experiences more of a specific kind of motor difficulty—or motor symptoms in general—when the patient has not slept well, as determined by self-reporting and/or sleep monitoring devices. As another example, the system may find a correlation between a patient feeling more depressed during times when the patient's social contacts are deteriorating. In some embodiments, certain such events and correlations may be specified for monitoring by a physician or patient. In some embodiments, a system may unilaterally detect events and/or correlations and choose which ones to track or report, for example by applying machine learning or other computing techniques to the gathered data.

Many neurological diseases are individual to each subject. Each subject with the same neurological disease can experience a unique progression of mobility impairment. Thus, a baseline biomarker profile that includes standard benchmarks for all subjects with same neurological disease may not provide the best rating scale for identifying a subject's unique progression of mobility impairment. In some embodiments, the biomarker tracking system 100 adjusts one or more of the standard benchmarks included in the baseline biomarker profile based on user input. User input may include, for example, a second rating for a vocal exercise provided by a doctor via the user interface 235. The electronic processor 220 may compare the second rating for the vocal exercise with the rating for the vocal exercise assigned by the electronic processor 220 to identify any differences. In some embodiments, the electronic processor 220 adjusts at least one of the plurality of benchmarks included in the baseline biomarker profile based on the determined difference between the two ratings for the vocal exercise.

The second rating for the vocal exercise may be received via the user interface 235 while the subject is performing the vocal exercise or immediately after. However, in order to remove the requirement for a doctor to be physically present while the subject is performing the vocal exercise, in some embodiments, all (or a portion) of the audio from the vocal exercises captured by the microphone 215 of the subject performing the vocal exercise is included in the session record 500 as vocal exercise data. Adding the audio from the vocal exercises to the session record 500 enables a doctor to view subject's performance of the vocal exercise and provide their own rating at a later time and at a different location.

Returning to FIG. 5, the mood data 535 includes data indicating non-vocal symptoms of the subject. As described above, some established rating scales for subjects with neurological diseases include questionnaires. For example, questionnaires such as the PD NMS questionnaire, the PDQ-39, and the PDQ-8 are utilized for subjects with Parkinson's disease. The PD NMS questionnaire is used to detect non-motor symptoms. The PDQ-39 and PDQ-8 are each a set of questions that are used to capture feedback from a subject regarding the subject's quality of life. In some embodiments, the electronic processor 220 administers a questionnaire to the subject by displaying questions on the display screen 135 and receiving the subject's responses via the user interface 235. The mood data 535 includes the subject's responses to a questionnaire. These questions may include, but are not limited to, questions about subjects sleep patterns, emotional well-being, mobility, bodily discomfort, cognitions, stigma, and activities of daily living. The mood data 535 is included in the session record 500 and in some embodiments may be used by the electronic processor 220 to help formulate the baseline biomarker model for a subject.

The speech data 540 includes, among other things, all (or any portion) of the sound recorded by the microphone 215 while the subject is performing the vocal exercise. Subjects with Parkinson's diseases (or other neurological diseases) can suffer from impaired speech. In some embodiment, the electronic processor 220 (or the server 110) analyzes the speech data 540 to identify any speech problems. For example, the electronic processor 220 may analyze the speech data 540 to identify any loss of modulation, diction, or volume. The speech data 540 may include but is not limited to, tremor detection data, speech volume data, pronunciation data, speech strength data, and changes in tonality, hesitance in voice, changes in speed, and changes in verbiage. Importantly, the speech data 540 may include data picked up during the vocal exercise which was outside of the vocal exercise itself such as background noise made by the subject. Such audio data may be additionally useful in formulation by the electronic processor 220 of the baseline biomarker model for a subject.

In some embodiments, the electronic processor 220 is cognizant of the current vocal exercise being performed by the subject prior to the subject performing it. For example, the electronic processor 220 may determine the current vocal exercise based on user input received via the user interface 235 or the transceiver 230. Alternatively or in addition, the electronic processor 220 identifies the current vocal exercise based on the loudness of speech picked up by the microphone 215. For example, by comparing the decibels of the subject's speech to a set of predetermined reference markers included in some embodiments of the baseline biomarker profile, the electronic processor 220 may determine that the subject is performing a speech strength or volume exercise.

As described above, current evaluation methods for subjects with Parkinson's disease require a doctor to be present to administer the evaluation. Thus, subjects with Parkinson's disease are typically evaluated only once or twice a year when during visits to their doctor. This frequency of evaluation does not provide doctors with enough information to make informed decisions about the efficacy of treatments being provided to subjects. By recording and automatically evaluating subjects' performances of vocal exercises, the biomarker tracking system 100 can be used to evaluate subjects with Parkinson's disease using established rating scales without requiring a doctor to be present. Not needed a doctor to be present enables evaluations to be conducted more often because a subject can perform the evaluations in their own home. More frequent evaluations enable better tracking of the progression of neurological diseases. More frequent evaluations also give doctors more information about the efficacy of different treatments and medications.

In addition, the biomarker tracking system 100 can be used to provide objectivity in evaluating subjects with Parkinson's disease. As described above, current evaluation methods utilize a doctor's judgements of a subject's performances of vocal exercises. On the other hand, the biomarker tracking system 100 rates a subject's performance of a vocal exercise by calculating attributes that cannot be accurately determined by a doctor's judgement, such as precise volume and pronunciation. Thus, the biomarker tracking system 100 brings objectivity to subjectivity in evaluating subjects with Parkinson's disease.

Further, the biomarker tracking system 100 can be used for early detection of neurological diseases. For Parkinson's disease, a subject's vocal patterns typically have already undergone changes in at least one of speech strength or pronunciation by the time a clinic diagnosis is made. The biomarker tracking system 100 can be used to identify decreases in a subject's vocal functions, which can be an early indicator of Parkinson's disease.

In some embodiments, the server 110 (or the electronic controller 140) includes (or implements) a machine learning engine that can assign a disease (or physical) state to a subject by evaluating a plurality of session records of the subject. The machine learning engine evaluates feedback from medical professionals (for example, a second rating for a vocal exercise provided by a doctor, annotated clinician report, etc.) to train a classifier of the machine learning engine. For example, in reference to Parkinson's disease, the machine learning engine matches the second rating for a vocal exercise provided by a doctor with the captured speech data 540 to train the classifier. The machine learning engine identifies and extracts raw vocal features associated with each vocal exercise. The machine learning engine models these raw vocal features collected from various subjects (including subjects in various disease states, control subjects who are healthy, or both) in order to differentiate between different ratings for vocal exercises, and to generate and adjust the plurality of benchmarks in the baseline biomarker profile. The biomarker tracking system 100 can use the machine learning engine to predict the neurological disease state (or present physical abnormality) of a subject in substantially real time using data captured by the biomarker tracking system 100 including, among other things, result data 515, subject state data 525, mood data 535, speech data 540, or a combination thereof.

Any of the functionality described above as being executed by a specific component of the electronic controller 140 in the electronic tracking device 105 may be performed, in whole or are in part, by one or more components of the server 110. For example, in some embodiments, the electronic controller 140 extracts the speech data, detects vocal patterns, determines attributes of the detected speech data, assigns a rating for the vocal exercise, and creates a session record for the subject. In other embodiments, the electronic controller 140 extracts and sends the speech data to the server 110, and the server 110 detects vocal patterns, determines attributes of the detected speech data, assigns a rating for the vocal exercise, and creates a session record for the subject.

Various embodiments and features are set forth in the following claims.

What is claimed is:

1. A system for tracking biomarkers, comprising:
a sensory array including a microphone;
a server for storing a baseline biomarker model; and
an electronic processor configured to:
  collect speech data generated by the sensor array and associated with a subject, the speech data comprising one or more of tremor detection data, speech volume and pronunciation data, and speech strength data;
  access the stored baseline biomarker model from the server;
  compare the speech data to the stored baseline biomarker model;
  receive subjective feedback related to the subject, the feedback data provided by one or more clinicians; and
  generate a speech data deviation model based, at least in part, on the comparison of the speech data to the stored baseline biomarker model and the received subjective feedback related to the subject.

2. The system of claim 1, wherein the electronic processor is configured to generate a disease state report based, at least in part, on the speech data deviation model.

3. The system of claim 2, wherein the disease state report is automatically reported to a third party.

4. The system of claim 3, wherein the generation of a disease state report further comprises considering one or more of medication intake timing, reported sleep data, and reported physical exercise.

5. The system of claim 2, wherein generating the disease state report further comprises receiving responses to a questionnaire, the responses collected by the electronic processor.

6. The system of claim 1, wherein the baseline biomarker model comprises previously collected data associated with the subject.

7. The system of claim 6, wherein the baseline biomarker model comprises speech data of a cohort of the subject.

8. The system of claim 1, wherein the baseline biomarker model is updated using one or more of the collected speech data of the subject and the speech deviation model.

9. The system of claim 1, wherein the electronic processor collects data over at least one week.

10. The system of claim 1, wherein the collected speech data further comprises one or more of changes in tonality, hesitance in voice, and changes in speed or verbiage.

11. A method for tracking biomarkers, comprising:
capturing tremor detection data, speech volume and pronunciation data, and speech strength data with a microphone;
storing a baseline biomarker model in an external server;
collecting tremor detection data, speech volume and pronunciation data, speech strength data, and subjective feedback data related to the subject, the feedback data provided by one or more clinicians;
accessing the stored baseline biomarker model from the external server;
comparing the tremor detection data, speech volume and pronunciation data, speech strength data, and subjective feedback data to the stored baseline biomarker model; and
generating a speech data error recognition percentage.

12. The method of claim 11, further comprising generating a disease state report by comparing the collected and stored data.

13. The method of claim 12, further comprising collecting a questionnaire by the electronic processor as data in generation of the disease state report.

14. The method of claim 13, further comprising generating a disease state report which includes linking voice parameters to other motor data such as medication intake timing, reported sleep data, and reported physical exercise.

15. The method of claim 14, further comprising engaging in adaptive learning based on the linked voice parameters and other motor data.

16. The system of claim 14, further comprising building a baseline profile using the complete disease state report.

17. The system of claim 16, further comprising monitoring the progression of a disease by detecting when data thresholds specific to a user's baseline profile are surpassed.

18. The method of claim 12, further comprising automatically reporting the state report to a third party.

19. The method of claim 11, further comprising collecting data over at least one week.

20. The method of claim 11, wherein collecting data further includes collecting changes in tonality, hesitance in voice, and changes in speed or verbiage.

* * * * *